United States Patent [19]

Berkner

[11] Patent Number: 5,288,629
[45] Date of Patent: Feb. 22, 1994

[54] DNA SEQUENCE ENCODING FACTOR VII WITH AN AMINO ACID SUBSTITUTION AT AVG-152

[75] Inventor: Kathleen L. Berkner, Seattle, Wash.

[73] Assignee: ZymoGenetics, Inc., Seattle, Wash.

[21] Appl. No.: 951,295

[22] Filed: Sep. 21, 1992

Related U.S. Application Data

[63] Continuation of Ser. No. 471,313, Jan. 29, 1990, abandoned.

[51] Int. Cl.$^5$ .................. C12N 5/00; C12N 15/00; C07H 15/12; C07H 17/00
[52] U.S. Cl. .................. 435/240.2; 536/23.1; 935/10
[58] Field of Search ............ 536/23.1; 435/69.6, 435/70.3, 240.2; 935/10

[56] References Cited

U.S. PATENT DOCUMENTS

| 4,775,624 | 10/1988 | Bang et al. |
|---|---|---|
| 4,784,950 | 11/1988 | Hagen ........................ 435/68 |
| 4,959,318 | 9/1990 | Foster et al. |
| 4,994,371 | 2/1991 | Davie et al. |

FOREIGN PATENT DOCUMENTS

| 255771 | 10/1988 | European Pat. Off. |
|---|---|---|
| 0296413 | 12/1988 | European Pat. Off. |
| 370036 | 6/1992 | European Pat. Off. |
| 8606408 | 11/1986 | World Int. Prop. O. |
| 8909612 | 10/1989 | World Int. Prop. O. |

OTHER PUBLICATIONS

Lee et al. (1983) Thromb. Res. 30, 511–519.
Hagen et al. (1986) PNAS 83, 2412–2416.
Pittman et al. (1988) PNAS 85, 2429–2433.
Kisiel et al., *Biochem.* 16:4189–4194 (1977).
Petersen et al., *FEBS Lett.* 114:278–282 (1980).
McRae et al., *Biochem.* 20:7196–7206 (1981).
Hojrup et al. (*Eur. J. Biochem.*) 126:343–348 (1982).
Lottenberg et al., *Thromb. Res.* 28:313–332 (1982).
Broze et al. (*J. Clin. Invest.*) 73:933–938 (1984).
Cho et al., *Biochem.* 23:644–650 (1984).
Leytus et al., *Biochem.* 25:5098–5102 (1986).
Foster et al., *Biochem.* 26:7003–7011 (1987).
Thim et al., *Biochem.* 27:7785–7793 (1988).
Sakai et al., *J. Biol. Chem.* 264:9980–9988 (1989).
Kurachi et al., *Proc. Natl. Acad. Sci. USA*, 79:6461–6464 (1982).
Degen et al., *Am. Chem. Soc.*, 22:2087–2097 (1983).
Leytus et al., *Proc. Natl. Acad. Sci. USA*, 81:3699–3702 (1984).
Foster et al., *Proc. Natl. Acad. Sci. USA*, 82:4673–4677 (1985).
Takeya et al., *J. Biol. Chem.*, 263:14868–14872 (1988).

Primary Examiner—Elizabeth C. Weimar
Assistant Examiner—Deborah Crouch
Attorney, Agent, or Firm—Townsend and Townsend Khourie and Crew

[57] ABSTRACT

Factor VII of the coagulation cascade is modified to act as an anticoagulant. Amino acid modifications are employed to produce a modified Factor VII having a substantially reduced susceptibility to activation by enzymes which typically activate wild-type Factor VII. The modified Factor VII is able to compete with wild-type Factor VII and/or VIIa for binding tissue factor, inhibiting clotting activity. As the modified Factor VII acts specifically to interrupt the coagulation cascade, pharmaceutical compositions of modified Factor VII may be administered in place of, or in conjunction with lower doses of, conventional anticoagulant therapies.

8 Claims, 4 Drawing Sheets

HUMAN

```
 145                 150    ↓       155
-ASN-ALA-SER-LYS-PRO-GLN-GLY-ARG-ILE-VAL-GLY-GLY-LYS-
```

BOVINE

```
 145                 150    ↓       155
-ASN-GLY-SER-LYS-PRO-GLN-GLY-ARG-ILE-VAL-GLY-GLY-HIS-
```

DNA SEQUENCE ENCODING FACTOR VII WITH AN AMINO ACID SUBSTITUTION AT AVG-152

This is a continuation of application Ser. No. 07/471,313 filed Jan. 29, 1990, now abandoned.

FIELD OF THE INVENTION

The present invention relates to proteins useful an anticoagulants. More specifically, the present invention relates to modified forms of Factor VII that inhibit blood coagulation.

BACKGROUND OF THE INVENTION

Blood coagulation is a process consisting of a complex interaction of various blood components, or factors, which eventually gives rise to a fibrin clot. Generally, the blood components which participate in what has been referred to as the coagulation "cascade" are proenzymes or zymogens, enzymatically inactive proteins which are converted to proteolytic enzymes by the action of an activator, itself an activated clotting factor. Coagulation factors that have undergone such a conversion and generally referred to as "active factors," and are designated by the addition of a lower case "a" suffix (e.g., Factor VIIa).

Activated Factor X ("Xa") is required to convert prothrombin to thrombin, which then converts fibrinogen to fibrin as a final stage in forming a fibrin clot. There are two systems, or pathways, that promote the activation of Factor X. The "intrinsic pathway" refers to those reactions that lead to thrombin formation through utilization of factors present only in plasma. A series of protease-mediated activations ultimately generates Factor IXa which, in conjunction with Factor VIIIa, cleaves Factor X into Xa. An identical proteolysis is effected by Factor VIIa and its co-factor, tissue factor, in the "extrinsic pathway" of blood coagulation. Tissue factor is a membrane bound protein and does not normally circulate in plasma. Upon vessel disruption, however, it can complex with Factor VIIa to Catalyze Factor X activation or Factor IX activation in the presence of $Ca^{++}$ and phospholipid (Nemerson and Gentry, Biochem. 25:4020–4033 (1986)). While the relative importance of the two coagulation pathways in hemostasis is unclear, in recent years Factor VII and tissue factor have been found to play a pivotal role in the regulation of blood coagulation.

Factor VII is a trace plasma glycoprotein that circulates in blood as a single-chain zymogen. The zymogen is catalytically inactive (Williams et al., J. Biol. Chem. 264:7536–7543 (1989); Rao et al., Proc. Natl. Acad. Sci. USA. 85:6687–6691 (1988)). Single-chain Factor VII may be converted to two-chain Factor VIIa by Factor Xa, Factor XIIa, Factor IXa or thrombin in vitro. Factor Xa is believed to be the major physiological activator of Factor VII. Like several other plasma proteins involved in hemostasis, Factor VII is dependent on vitamin K for its activity, which is required for the γ-carboxylation of multiple glutamic acid residues that are clustered in the amino terminus of the protein. These γ-carboxylated glutamic acids are required for the metal-associated interaction of Factor VII with phospholipids.

The conversion of zymogen Factor VII into the activated two-chain molecule occurs by cleavage of an internal peptide bond located approximately in the middle of the molecule. In human Factor VII, the activation cleavage site is at $Arg_{152}$–$Ile_{153}$ (Hagen et al., Proc. Natl. Acad. Sci. USA 83: 2412–2416 (1986)). Bovine factor VII is activated by cleavage at the analogous $Arg_{152}$–$Ile_{153}$ bond (Takeya et al., J. Biol. Chem. 263: 14868–14877, 1988). In the presence of tissue factor, phospholipids and calcium ions, the two-chain Factor VIIa rapidly activates Factor X or Factor IX by limited proteolysis.

It is often necessary to selectively block the coagulation cascade in a patient. Anticoagulants such as heparin, coumarin, derivatives of coumarin, indandione derivatives, or other agents may be used, for example, during kidney dialysis, or to treat deep vein thrombosis, disseminated intravascular coagulation (DIC), and a host of other medical disorders. For example, heparin treatment or extracorporeal treatment with citrate ion (U.S. Pat. No. 4,500,309) may be used in dialysis to prevent coagulation during the course of treatment. Heparin is also used in preventing deep vein thrombosis in patients undergoing surgery.

Treatment with heparin and other anticoagulants may, however, have undesirable side effects. Heparin may cause heavy bleeding. Furthermore, with a half-life of approximately 80 minutes, heparin is rapidly cleared from the blood, necessitating frequent administration. Because heparin acts as a cofactor for antithrombin III (AT III), and antithrombin III is rapidly depleted in DIC treatment, it is often difficult to maintain the proper heparin dosage, necessitating continuous monitoring of AT III and heparin levels. Heparin is also ineffective if AT III depletion is extreme. Further, prolonged use of heparin may also increase platelet aggregation and reduce platelet count, and has been implicated in the development of osteoporosis. Indandione derivatives may also have toxic side effects.

In addition to the anticoagulants briefly described above, several naturally occurring proteins have been found to have anticoagulant activity. For example, Reutelingsperger (U.S. Pat. No. 4,736,018) isolated anticoagulant proteins from bovine aorta and human umbilical vein arteries. Maki et al. (U.S. Pat. No. 4,732,891) disclose human placenta-derived anticoagulant proteins. In addition, antithrombin III has been proposed as a therapeutic anticoagulant (Schipper et al., Lancet 1 (8069): 854–856 (1978 ); Jordan, U.S. Pat. No. 4,386,025; Bock et al., U.S. Pat. No. 4,517,294).

There is still a need in the art for improved compositions having anticoagulant activity which do not produce the undesirable side effects associated with traditional anticoagulant compositions. The present invention fulfills this need, and further provides other related advantages.

SUMMARY OF THE INVENTION

Novel compositions which comprise modified Factor VII having anticoagulant properties are provided. The Factor VII sequence has at least one amino acid modification, where the modification is selected so as to substantially reduce the susceptibility of Factor VII to activation by plasma factors, such as Xa, and is capable of inhibiting the clotting activity of wild-type Factor VIIa. The novel Factor VII may have a modified activation region, in some instances at the dipeptide which forms the cleavage site of the activation region. Thus, the modified Factor VII molecule is substantially resistant to activation by Factor VII activators present in plasma or tissues, such as Factor XIIa, Factor IXa, Factor Xa or thrombin, but particularly Xa and IXa.

The modified Factor VII is capable of binding tissue factor. The modified Factor VII compositions are typically in substantially pure form.

The compositions of the invention are particularly useful in methods for treating patients when formulated into pharmaceutical compositions, where they may be given to individuals suffering from a variety of disease states to treat coagulation-related conditions. Such modified Factor VII molecules, having increased resistance to activation by plasma, may possess a longer plasma half-life and thus a correspondingly longer period of anticoagulative activity when compared to other anticoagulants. Among the medical indications for the subject compositions are those commonly treated with anticoagulants, such as, for example, deep vein thrombosis, pulmonary embolism, stroke, disseminated intravascular coagulation (DIC) and myocardial infarction.

Typically, for administration to humans the pharmaceutical compositions will comprise modified human Factor VII protein and pharmaceutically-acceptable carriers and buffers.

In certain preferred embodiments in human and bovine Factor VII, the modified cleavage site residues are $Arg_{152}$ and/or $Ile_{153}$. Preferably $Arg_{152}$ is changed to an amino acid not having a positive charge, preferably Glu, Leu or Asp. $Ile_{153}$ can be replaced with a charged or bulky heterocyclic aromatic amino acid.

In another embodiment the invention concerns a recombinant zymogen modified Factor VII molecule comprising one or more amino acid substitutions in the activation region, preferably at or near the cleavage site, which thereby renders the modified Factor VII molecule substantially resistant to activation at its cleavage site.

In another aspect the invention relates to a polynucleotide molecule comprising two operatively linked sequence coding regions encoding, respectively, a pre-pro peptide and a gla domain of a vitamin K-dependent plasma protein, and a gla domain-less Factor VII protein, wherein upon expression said polynucleotide encodes a modified Factor VII molecule which is not substantially activated by plasma Factor Xa or IXa and is capable of binding tissue factor. The modified Factor VII molecule expressed by this polynucleotide is a biologically active anticoagulant, that is, it is capable of inhibiting the coagulation cascade and thus the formation of a fibrin deposit or clot. To express the modified Factor VII the polynucleotide molecule is transfected into mammalian cell lines, such as BHK, BHK 570 or 293 cell lines.

BRIEF DESCRIPTION OF THE FIGURES

FIGS. 2a and 2b: Construction of the $Arg_{152} \rightarrow Glu$ Factor VII expression plasmid. The Arg to Glu mutation introduced into Factor VII is indicated by the bold type within the sequence shown for two of the six oligonucleotides used to synthesize the Xba I-Nco I Factor VII cDNA fragment. The numbering for the cDNA is for the 38-amino acid leader form of Factor VII (Hagen et al., *Proc. Natl. Acad. Sci. USA* 83:2412-2416 (1986), incorporated herein by reference). The abbreviations for the expression vector are as follows: 0-1 represents the left-most 350 bp of adenovirus 5; E, the SV40 enhancer sequences; MLP and L1-3, the major late promotor and tripartite leader, respectively, of adenovirus 2; 5'ss and 3'ss, a splice signal cassette; and pA, the SV40 early polyadenylation signal. The 0.7 Kb Eco RI-Sst I fragment subcloned into M13mp19 is indicated by a bracket at the bottom of the figure. The arrow represents the actual region of Factor VII that was sequenced.

DESCRIPTION OF THE SPECIFIC EMBODIMENTS

Novel modified Factor VII having anticoagulant activity is provided by the present invention. Compositions of the modified Factor VII are suitable for administration to a variety of mammals, particularly humans, to inhibit the coagulation cascade. Modified Factor VII may be administered to a patient in conjunction with or in place of other anticoagulant compounds.

Figure 1:
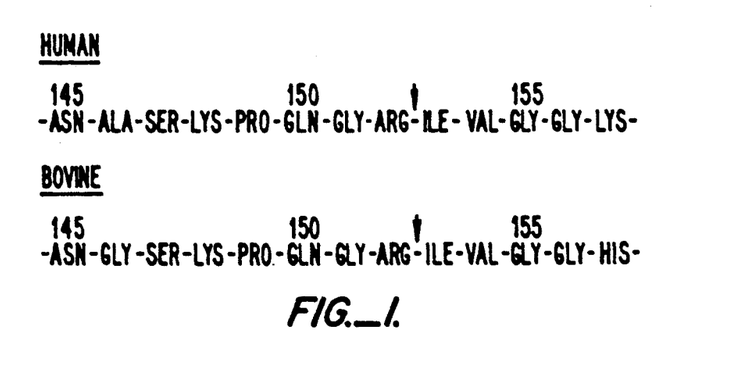
FIG. 1: The amino acid sequences around the cleavage sites of human and bovine Factor VII. Amino acids are numbered from the first amino acid of the mature zymogen. Cleavage between amino acids 152 and 153 (arrow) results in formation of the activated protein.

Factor VII plays an important role in the coagulation cascade, particularly that involving the extrinsic pathway. Present in the circulating plasma as an inactive single chain zymogen protein, cleavage of a dipeptide bond in the activation region leads to two polypeptides, light and heavy chains, which are held together by at least one disulfide bond. A variety of plasma factors may activate Factor VII, such as Factors Xa, XIIa, IXa or thrombin. Once activated, Factor VIIa combines with tissue factor in the presence of calcium ions to activate Factor X to Xa, and acts in the intrinsic pathway to activate Factor IX to IXa, with the eventual formation of a fibrin clot.

The present invention provides the ability to inhibit this sequence of events in the coagulation cascade by preventing or otherwise inhibiting the activation of Factor VII. Modified Factor VII proteins that are resistant to activation have been found to compete with native Factor VII and/or VIIa for binding to tissue factor. As a result, the activation of Factors X and IX is inhibited.

According to the present invention the activation of Factor VII is inhibited by substituting, inserting or deleting amino acids. In preferred embodiments the amino acid sequence modifications are made in the Factor VII activation region, defined herein as the region containing the peptide bond which is cleaved to form the two-chain Factor VIIa, and up to about four amino acids in the N-terminal direction and up to about four amino acids in the C-terminal direction from the bond. The substitutions, insertions or deletions in the activation region are generally at or adjacent to the cleavage site between the heavy and light chains. The cleavage site is thus defined herein as two or more amino acids with a covalent bond between them, which bond is cleaved in zymogen Factor VII to produce two-chain Factor VIIa. In the human and bovine Factor VII proteins, this cleavage site is defined by amino acids $Arg_{152}$ and $Ile_{153}$ (subscript numbering indicating position in the sequence; see FIG. 1). Cleavage of the peptide bond between these two residues generates the active form of the protein. The cleavage sites, and thus the activation regions as herein defined, in Factor VII preparations from other mammalian species may be determined using presently available techniques, including protein isolation and amino acid sequence analysis. The amino acid substitutions, insertions or deletions are made so as to prevent or otherwise inhibit cleavage by enzymes which typically activate Factor VII, such as Xa, XIIa, IXa or thrombin. The modified Factor VII, however, should also retain the ability to compete with authentic Factor VII and/or Factor VIIa for binding in the coagulation cascade. Such competition may readily be determined by means of a clotting assay, described herein, or a competition binding assay using, e.g. a cell line having cell-surface tissue factor, such as the human bladder carcinoma cell line J82 (Sakai et al. *J. Biol. Chem.* 264: 9980–9988 (1989), incorporated by reference herein.)

The amino acids forming the peptide bond at the cleavage site in authentic Factor VII, such as $Arg_{152}$ and $Ile_{153}$ in human and bovine Factor VII, may either be substituted or deleted, or an additional amino acid(s) inserted at the cleavage site. Within the present invention, it is preferred to change only a single amino acid, thus minimizing the likelihood of increasing the antigenicity of the molecule or inhibiting its ability to bind tissue factor, however two or more amino acid changes (substitutions, additions or deletions) may be made. Combinations of substitutions(s), additions(s) and deletion(s) may also be made. In a preferred embodiment, the change(s) is (are) made in the activation region, i.e., within about four amino acids of the cleavage site amino acids P4 through P4'; see Table 1 below). It is most preferred to change one of the amino acids adjacent to the cleavage site, i.e., either $Arg_{152}$ or $Ile_{153}$ in the case of human and bovine Factor VII. For example, in a preferred embodiment for human or bovine Factor VII, $Arg_{152}$ is deleted or substituted. It is preferred to substitute an amino acid other than Lys for Arg, and in a most preferred embodiment, Glu is substituted for Arg. Other preferred substitutions are Leu, Asp, Gly, Ile and uncharged or aromatic amino acids. $Ile_{153}$ can be replaced with another amino acid, preferably a charged (e.g., Glu, Asp, His, Lys) or bulky, heterocyclic aromatic (e.g. Tyr, Phe, Trp) amino acid. Other modified forms of Factor VII provided by the present invention include those in which the amino acid in the P2 position is replaced by an amino acid other than Phe. Representative modifications of the amino acid sequence in the activation region and near or at the cleavage site of human Factor VII are set forth in Table 1.

TABLE 1

| | $P_4$ | $P_3$ | $P_2$ | $P_1$ | $P_1'$ | $P_2'$ | $P_3'$ | $P_4'$ |
|---|---|---|---|---|---|---|---|---|
| Native human Factor VII: | Pro—Gln—Gly—Arg—Ile—Val—Gly—Gly |
| | Pro—Gln—Gly—-—Ile—Val—Gly—Gly |
| | Pro—Gln—Gly—Glu—Ile—Val—Gly—Gly |
| | Pro—Gln—Gly—Leu—Ile—Val—Gly—Gly |
| | Pro—Gln—Gly—Asp—Ile—Val—Gly—Gly |
| | Pro—Gln—Gly—Asp—Tyr—Val—Gly—Gly |

As the cleavage sites for the plasma activators of Factor VII (generally considered to be arginine-specific proteases) are identified in Factor VII from different mammalian species, one may introduce residue alterations as described above in the appropriate Factor VII sequence and test the resulting protein for the desired level of resistance to activation as described herein. In addition, synthetic peptide substrates may be prepared and tested for their interaction with Factor IXa, Factor Xa, Factor XIIa and thrombin as generally described by McRae et al., *Biochem.* 20: 7196–7206 (1981) and Cho et al. *Biochem.* 23: 644–650 (1984) incorporated herein by reference.

The proteins of the present invention may be produced through the use of recombinant DNA techniques. In general, a cloned wild-type Factor VII DNA sequence is modified to encode the desired protein. This modified sequence is then inserted into an expression vector, which is in turn transformed or transfected into host cells. Higher eukaryotic cells, in particular cultured mammalian cells, are preferred as host cells. The complete nucleotide and amino acid sequences for human Factor VII are known. See U.S. Pat. No. 4,784,950, which is incorporated herein by reference, where the cloning and expression of recombinant human Factor VII is described. The bovine Factor VII sequence is described in Takeya et al., *J. Biol. Chem.* 263:14868–14872 (1988), which is incorporated by reference herein.

The sequence alterations may be accomplished by a variety of techniques. Modification of the DNA sequence may be by site-specific mutagenesis. Techniques for site-specific mutagenesis are well known in the art and are described by, for example, Zoller and Smith (*DNA* 3:479–488, 1984). Alternatively, the DNA sequence may be enzymatically cleaved to remove the native cleavage site sequence, and the sequences encoding the heavy and light chains joined to a synthesized DNA sequence encoding one of the altered cleavage sites or activation regions described above. Thus, using the nucleotide and amino acid sequences of Factor VII, one may introduce the alteration(s) of choice.

The Factor VII modified according to the present invention includes those proteins that have the amino-terminal portion (gla domain) substituted with a gla domain of one of the vitamin-K dependent plasma proteins Factor IX, Factor X, prothrombin, protein C, protein S or protein Z. Methods for producing Factor VII with a heterologous gla domain are disclosed in U.S. Pat. No. 4,784,950 incorporated by reference herein.

DNA sequences for use within the present invention will encode a pre-pro peptide at the amino-terminus of the Factor VII protein to obtain proper post-translational processing (e.g. gamma-carboxylation of glutamic acid residues) and secretion from the host cell. The pre-pro peptide may be that of Factor VII or another vitamin K-dependent plasma protein, such as Factor IX, Factor X, prothrombin, protein C or protein S. It is generally preferred that the pre-pro peptide and gla domain be obtained from the same protein. As will be appreciated by those skilled in the art, additional modifications can be made in the amino acid sequence of the modified Factor VII where those modifications do not significantly impair the ability of the protein to act as an anticoagulant.

Expression vectors for use in carrying out the present invention will comprise a promoter capable of directing the transcription of a cloned gene or cDNA. Preferred promoters for use in cultured mammalian cells include viral promoters and cellular promoters. Viral promoters include the SV40 promoter (Subramani et al., *Mol. Cell. Biol.* 1:854-864, 1981) and the CMV promoter (Boshart et al., *Cell* 41:521-530, 1985). A particularly preferred viral promoter is the major late promoter from adenovirus 2 (Kaufman and Sharp, *Mol. Cell. Biol.* 2:1304-1319, 1982). Cellular promoters include the mouse kappa gene promoter (Bergman et al., *Proc. Natl. Acad. Sci. USA* 81:7041-7045 1983) and the mouse $V_H$ promoter (Loh et al., *Cell* 33:85-93, 1983). A particularly preferred cellular promoter is the mouse metallothionein-I promoter (Palmiter et al., *Science* 222:809-814, 1983). Expression vectors may also contain a set of RNA splice sites located downstream from the promoter and upstream from the insertion site for the Factor VII sequence itself. Preferred RNA splice sites may be obtained from adenovirus and/or immunoglobulin genes. Also contained in the expression vectors is a polyadenylation signal located downstream of the insertion site. Particularly preferred polyadenylation signals include the early or late polyadenylation signal from SV40 (Kaufman and Sharp, ibid.), the polyadenylation signal from the adenovirus 5 E1b region, the human growth hormone gene terminator (DeNoto et al. *Nuc. Acids Res.* 9:3719-3730, 1981) or the polyadenylation signal from the human Factor VII gene or the bovine Factor VII gene. The expression vectors may also include a noncoding viral leader sequence, such as the adenovirus 2 tripartite leader, located between the promoter and the RNA splice sites; and enhancer sequences, such as the SV40 enhancer.

Cloned DNA sequences are introduced into cultured mammalian cells by, for example, calcium phosphate-mediated transfection (Wigler et al., *Cell* 14:725-732, 1978; Corsaro and Pearson, *Somatic Cell Genetics* 7:603-616, 1981; Graham and Van der Eb, *Virology* 52d:456-467, 1973) or electroporation (Neumann et al., *EMBO J.* 1:841-845, 1982). To identify and select cells that express the exogenous DNA, a gene that confers a selectable phenotype (a selectable marker) is generally introduced into cells along with the gene or cDNA of interest. Preferred selectable markers include genes that confer resistance to drugs such as neomycin, hygromycin, and methotrexate. The selectable marker may be an amplifiable selectable marker. A preferred amplifiable selectable marker is a dihydrofolate reductase (DHFR) sequence. Selectable markers are reviewed by Thilly (*Mammalian Cell Technology*, Butterworth Publishers, Stoneham, Mass., incorporated herein by reference). The choice of selectable markers is well within the level of ordinary skill in the art.

Selectable markers may be introduced into the cell on a separate plasmid at the same time as the gene of interest, or they may be introduced on the same plasmid. If on the same plasmid, the selectable marker and the gene of interest may be under the control of different promoters or the same promoter, the latter arrangement producing a dicistronic message. Constructs of this type are known in the art (for example, Levinson and Simonsen, U.S. Pat. No. 4,713,339). It may also be advantageous to add additional DNA, known as "carrier DNA," to the mixture that is introduced into the cells.

After the cells have taken up the DNA, they are grown in an appropriate growth medium, typically 1-2 days, to begin expressing the gene of interest. As used herein the term "appropriate growth medium" means a medium containing nutrients and other components required for the growth of cells and the expression of the modified Factor VII gene. Media generally include a carbon source, a nitrogen source, essential amino acids, essential sugars, vitamins, salts, phospholipids, protein and growth factors. For production of gamma-carboxylated modified Factor VII, the medium will contain vitamin K, preferably at a concentration of about 0.1 $\mu$g/ml to about 5 $\mu$g/ml. Drug selection is then applied to select for the growth of cells that are expressing the selectable marker in a stable fashion. For cells that have been transfected with an amplifiable selectable marker the drug concentration may be increased to select for an increased copy number of the cloned sequences, thereby increasing expression levels. Clones of stably transfected cells are then screened for expression of modified Factor VII.

Preferred mammalian cell lines for use in the present invention include the COS-1 (ATCC CRL 1650), baby hamster kidney (BHK) and 293 (ATCC CRL 1573; Graham et al., *J. Gen. Virol.* 36:59-72, 1977) cell lines. A preferred BHK cell line is the tk⁻ ts13 BHK cell line (Waechter and Baserga, *Proc. Natl. Acad. Sci. USA* 79:1106-1110, 1982, incorporated herein by reference), hereinafter referred to as BHK 570 cells. The BHK 570 cell line has been deposited with the American Type Culture Collection, 12301 Parklawn Dr., Rockville, Md. 20852, prior to the filing of this patent application under ATCC accession number CRL 10314. A tk⁻ ts13 BHK cell line is also available from the ATCC under accession number CRL 1632. In addition, a number of other cell lines may be used within the present invention, including Rat Hep I (ATCC CRL 1600), Rat Hep II (ATCC CRL 1548), TCMK (ATCC CCL 139), Human lung (ATCC HB 8065), NCTC 1469 (ATCC CCL 9.1), CHO (ATCC CCL 61) and DUKX cells (Urlaub and Chasin, *Proc. Natl. Acad. Sci. USA* 77:4216-4220, 1980).

Modified Factor VII produced according to the present invention may be purified by affinity chromatography on an anti-Factor VII antibody column. The use of calcium-dependent monoclonal antibodies, as described by Wakabayashi et al. *J. Biol. Chem.* 261:11097-11108, (1986) and Thim et al., *Biochem.* 27: 7785-7793, (1988), is particularly preferred. Additional purification may be achieved by conventional chemical purification means, such as high performance liquid chromatography. Other methods of purification, including barium citrate precipitation, are known in the art, and may be applied to the purification of the novel modified Factor VII described herein (see, generally, Scopes, R., *Protein Purification*, Springer-Verlag, N.Y., 1982). Substantially pure modified Factor VII of at least about 90 to 95% homogeneity is preferred, and 98 to 99% or more homogeneity most preferred, for pharmaceutical uses. Once purified, partially or to homogeneity as desired, the modified Factor VII may then be used therapeutically.

The modified Factor VII molecules of the present invention and pharmaceutical compositions thereof are particularly useful for administration to humans to treat a variety of conditions involving intravascular coagulation. For instance, although deep vein thrombosis and pulmonary embolism can be treated with conventional anticoagulants, the modified Factor VII described herein may be used to prevent the occurrence of thromboembolic complications in identified high risk patients, such as those undergoing surgery or those with congestive heart failure. Since modified Factor VII is more selective than heparin, being active in the body generally only in the presence of tissue factor, and because modified Factor VII does not destroy other coagulation proteins, it will be more effective and less likely to cause bleeding complications than heparin when used prophylactically for the prevention of deep vein thrombosis. The dose of modified Factor VII for prevention of deep vein thrombosis is in the range of about 500 µg to 25 mg/day, preferably 5 to 15 mg/day for a 70 kg patient, and administration should begin at least about 6 hours prior to surgery and continue at least until the patient becomes ambulatory. In established deep vein thrombosis and/or pulmonary embolism, the dose of modified Factor VII ranges from about 500 µg to 25 mg as a loading dose followed by maintenance doses ranging from 1.5 to 15 mg/day, depending on the weight of the patient and the severity of the condition. Because of the lower likelihood of bleeding complications from modified Factor VII infusions, modified Factor VII can replace or lower the dose of heparin during or after surgery in conjunction with thrombectomies or embolectomies.

The modified Factor VII compositions of the present invention will also have substantial utility in the prevention of cardiogenic emboli and in the treatment of thrombotic strokes. Because of its low potential for causing bleeding complications and its selectivity, modified Factor VII can be given to stroke victims and may prevent the extension of the occluding arterial thrombus. The amount of modified Factor VII administered will vary with each patient depending on the nature and severity of the stroke, but doses will generally be in the range of those suggested below.

Pharmaceutical compositions of modified Factor VII provided herein will be a useful treatment in acute myocardial infarction because of the ability of modified Factor VII to inhibit in vivo coagulation. Modified Factor VII can be given with tissue plasminogen activator or streptokinase during the acute phases of the myocardial infarction. In acute myocardial infarction, the patient is given a loading dose of at least about 2 to 25 mg of modified Factor VII, followed by maintenance doses of about 1.5 to about 15 mg/day.

The modified Factor VII of the present invention is useful in the treatment of disseminated intravascular coagulation (DIC). Patients with DIC characteristically have widespread microcirculatory thrombi and often severe bleeding problems which result from consumption of essential clotting factors. Because of its selectivity, modified Factor VII will not aggravate the bleeding problems associated with DIC, as do conventional anticoagulants, but will retard or inhibit the formation of additional microvascular fibrin deposits.

The pharmaceutical compositions are intended for parenteral, topical, oral or local administration for prophylactic and/or therapeutic treatment. Preferably, the pharmaceutical compositions are administered parenterally, i.e., intravenously, subcutaneously, or intramuscularly. Thus, this invention provides compositions for parenteral administration which comprise a solution of the modified Factor VII molecules dissolved in an acceptable carrier, preferably an aqueous carrier. A variety of aqueous carriers may be used, e.g., water, buffered water, 0.4% saline, 0.3% glycine and the like. These compositions may be sterilized by conventional, well known sterilization techniques. The resulting aqueous solutions may be packaged for use or filtered under aseptic conditions and lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, etc. The concentration of modified Factor VII in these formulations can vary widely, i.e., from less than about 0.5%, usually at or at least about 1% to as much as 15 or 20% by weight and will be selected primarily by fluid volumes, viscosities, etc., in accordance with the particular mode of administration selected.

Thus, a typical pharmaceutical composition for intravenous infusion could be made up to contain 250 ml of sterile Ringer's solution, and 10 mg of modified Factor VII. Actual methods for preparing parenterally administrable compounds will be known or apparent to those skilled in the art and are described in more detail in for example, *Remington's Pharmaceutical Science*, 16th ed., Mack Publishing Company, Easton, Pa. (1982), which is incorporated herein by reference.

The compositions containing the modified Factor VII molecules can be administered for prophylactic and/or therapeutic treatments. In therapeutic applications, compositions are administered to a patient already suffering from a disease, as described above, in an amount sufficient to cure or at least partially arrest the disease and its complications. An amount adequate to accomplish this is defined as "therapeutically effective dose." Amounts effective for this use will depend on the severity of the disease or injury and the weight and general state of the patient, but generally range from about 0.5 mg to about 25 mg of modified Factor VII per day for a 70 kg patient, with dosages of from about 1.5 mg to about 15 mg of modified Factor VII per day being more commonly used. It must be kept in mind that the materials of the present invention may generally be employed in serious disease or injury states, that is, life-threatening or potentially life threatening situations. In such cases, in view of the minimization of extraneous substances and general lack of immunogenicity of modified human Factor VII in humans, it is possible and may be felt desireable by the treating physician to administer substantial excesses of these modified Factor VII compositions.

In prophylactic applications, compositions containing the modified Factor VII are administered to a patient susceptible to or otherwise at risk of a disease state or injury to enhance the patient's own anticoagulative capabilities. Such an amount is defined to be a "prophylactically effective dose." In this use, the precise amounts again depend on the patient's state of health and weight, but generally range from about 0.25 mg to about 25 mg per 70 kilogram patient, more commonly from about 1.5 mg to about 15 mg per 70 kg of body weight.

Single or multiple administrations of the compositions can be carried out with dose levels and pattern being selected by the treating physician. For ambulatory patients requiring daily maintenance levels, the modified Factor VII may be administered by continuous infusion using a portable pump system, for example. In any event, the pharmaceutical formulations should provide a quantity of modified Factor VII of this invention sufficient to effectively treat the patient.

The following examples are offered by way of illustration, not by way of limitation.

EXAMPLE I

Expression of $Arg_{152} \rightarrow Glu_{152}$ Factor VII

Figure 2A:
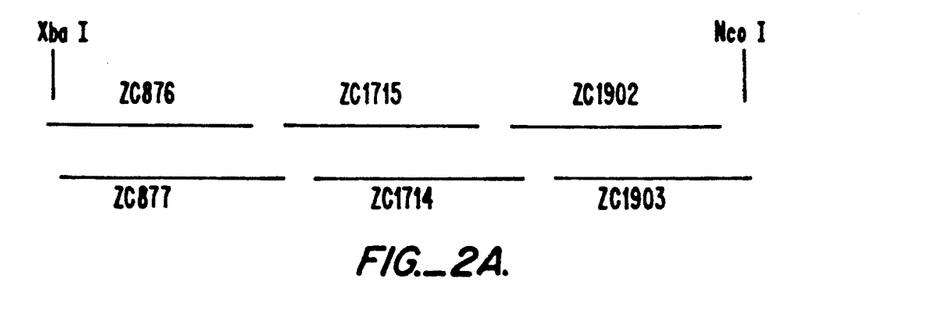
Figure 2B:
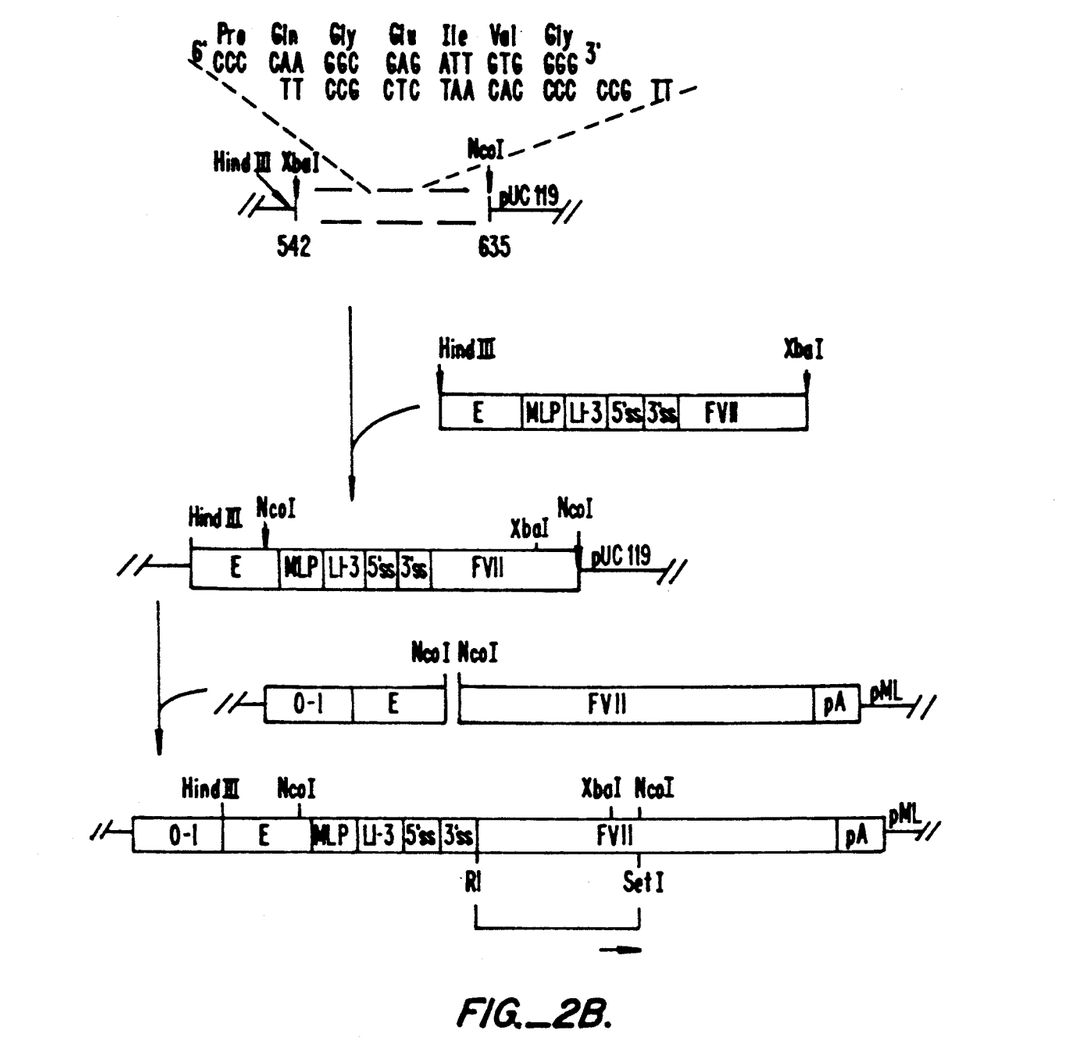

To generate the $Arg_{152} \rightarrow Glu$ Factor VII (R152E Factor VII) activation cleavage site mutant, the vector pUC119 (Vieira and Messing, *Meth. Enzymol.* 153: 3–11 (1987)) was first modified using oligonucleotide adapters to insert an Nco I cleavage site between the Xba I and Bam HI sites in the polylinker sequences. This manipulation and subsequent steps described below were performed according to standard protocols (Maniatis et al., *Molecular Cloning, A Laboratory Manual*, Cold Spring Harbor (1982)). Six oligonucleotides (see Table 2) comprising the Factor VII cDNA sequences between the Xba I site at 562 basepairs (bp) and the Nco I site at 635 bp (FIG. 2a) were then ligated into this pUCI19-derived vector (FIG. 2b). The oligonucleotides encoded a sequence identical to that of native Factor VII except for the substitution of a glutamic acid for arginine at amino acid 152.

TABLE 2

| Oligonucleotide | Sequence (5' → 3') |
|---|---|
| ZC876 | CTA GAA AAA AGA AAT GCC AGC AAA |
| ZC877 | GGG GTT TGC TGG CAT TTC TTT TTT |
| ZC1714 | TTG CCC CCC ACA ATC TCG CCT T |
| ZC1715 | CCC CAA GGC GAG ATT GTG GGG |
| ZC1902 | GGC AAG GTG TGC CCC AAA GGG GAG TGT C |
| ZC1903 | CAT GGA CAC TCC CCT TTG GGG CAC ACC |

The Factor VII/pUCI19 plasmid was cleaved with Hind III and Xba I, and a 1.6 kb fragment from plasmid FVII (565+2463)/pDX (U.S. Pat. No. 4,784,950; deposited with American Type Culture Collection under accession number 40205) containing part of the mammalian expression vector pDX (Foster et al., *Biochem.* 26: 7003–7011 (1987)) and the 5'-terminal portion of the Factor VII cDNA was then inserted into this DNA. The product of this ligation (FIG. 2b) was subsequently used to isolate a 1.4 kb Nco I fragment containing the mutated Factor VII sequences and part of the expression vector. This Nco I fragment was ligated to a 5.2 kb Nco I fragment from FVII (565+2463)/pDX containing the remainder of the Factor VII cDNA and mammalian expression vector. The DNA product, FVII (E152)/pDX, was checked for correct insert orientation using restriction enzyme analysis. To confirm that this plasmid contained the arginine to glutamic acid substitution at amino acid 152, a 0.7 kb Eco RI-Sst I fragment was isolated from FVII(E152)/pDX DNA and subcloned into M13mp19 DNA (Norrander et al., *Gene* 26 101–106, (1985)). The entire sequence between the Xba I site and the Nco I site of Factor VII (i.e., bp 562-bp 635) was determined by dideoxy-sequencing (Sanger et al., *Proc. Natl. Acad. Sci. USA* 74: 3642–3646, (1977)). The expected mutation corresponding to amino acid 152 was confirmed, and no other sequences were found to differ from that of native Factor VII.

The FVII(E152)/pDX DNA (10 μg) was cotransfected into BHK 570 cells with a plasmid (1 μg) encoding a mouse dihydrofolate reductase cDNA in pD5 (Berkner and Sharp, *Nucl. Acids Res.* 13: 841–857, (1985)). The BHK cells were maintained for two days in Dulbecco's modified Eagle's media (DMEM) containing 10% fetal calf serum and penicillin-streptomycin (Gibco), and were split at a 1:10 dilution into the same media supplemented with 150 nM methotrexate. After five days, the cells were fluid changed, and after an additional five days, colonies were clearly visible. A dozen individual colonies were isolated and clonally expanded. To confirm that these BHK cell lines expressed only the R152E Factor VII, genomic DNA was isolated from several of the cell lines and subjected to Southern analysis using an oligonucleotide (ZC1715) that distinguished the mutated sequences from native Factor VII DNA. Only the mutated Factor VII sequences were observed.

Individual colonies were screened for levels of production and for barium citrate precipitability. The BHK clones expressed Factor VII at levels between 1 and 5 μg/ml/day, as measured by an ELISA using a slight modification of the procedure developed by Engvall, *Meth. Enzymol.* 70: 419–439 (1980). An anti-Factor VII murine monoclonal antibody (AD-4) produced in Balb/c mice essentially according to Kohler and Milstein, *Nature* 256: 495–497 (1975) and purified from ascites fluid by a combination of DEAE-Affi-Gel Blue column chromatography (Bruck et al., *J. Immunol. Meth.* 53: 313–319 (1982)) and Sephadex G-150 column chromatography was employed to catch the Factor VII, and affinity-purified rabbit anti-Factor VII and peroxidase-conjugated goat anti-rabbit IgG were used to quantitate it. Protein concentrations were determined from various dilutions of normal pooled plasma assuming a plasma concentration of 400 ng Factor VII/ml (Fair, *Blood* 62: 784–791 (1983)). To assess γ-carboxylation of the recombinant protein, the Factor VII expression BHK lines, as well as B4A1, a BHK line expressing native recombinant Factor VII, were labeled in vivo with $^{35}$S-cysteine in modified Dulbecco's cysteine-free media containing 1% sodium pyruvate, 1% dialyzed fetal calf serum, 1% glutamine and 5 μg/ml vitamin K. Secreted material was harvested after 6 hours and subjected to barium citrate precipitation (Malhotra, *Thrombosis Res.* 15: 427–439 (1979)) followed by immunoprecipitation using an anti-Factor VII monoclonal antibody. R152E Factor VII quantitatively bound to barium citrate. In control experiments where vitamin K was omitted from the cell culture media, none of the Factor VII was adsorbed by barium citrate. When the immunoprecipitated samples were analyzed by SDS-PAGE under reducing conditions, the molecular weight of the R152E Factor VII was indistinguishable from native, wild-type Factor VII. These data indicate that the mutant protein was produced in the correctly processed mature form.

Approximately $6.0 \times 10^8$ cells from a representative Factor VII producing cell line were cultured in DMEM containing 1% dialyzed fetal calf serum, penicillin-streptomycin and 0.5 μg/ml vitamin K. The cells were cultured for up to 3 weeks and the culture supernatants harvested at approximately five day intervals. The culture supernatants (~750 ml) were centrifuged to remove potential cell debris and dialyzed overnight at 4° C. against 50 L of 10 mM Tris-HCl (pH 8.0) containing 150 mM NaCl. The retentate was made 10 mM in CaCl$_2$ and allowed to stand at 4° C. for 30 min. The calcified solution was centrifuged for 15 minutes at 30,000 xg, and the small button pellet discarded. The supernatant was applied to a calcium dependent anti-Factor VII monoclonal antibody (Thim et al., Biochem. 27: 7785-7793, (1988)) Sepharose column equilibrated with 10 mM Tris-HCl (pH 8.0)/ 10 mM CaCl$_2$ to remove protein non-specifically bound to the column. R152E Factor VII was then eluted from the column with 10 mM Tris-HCl (pH 8.0) containing 150 mM NaCl and 40 mM EDTA. The EDTA-eluted Factor VII fractions were pooled on the basis of Factor VII antigen concentration as determined by ELISA. The pooled material was concentrated by ultrafiltration (using a YM-10 membrane, Amicon, Danvers, Mass.) and dialyzed against either 0.05M Tris-HCl/ 0.1M NaCl (pH 7.5) or 1.0M NH$_4$HCO$_3$ (pH 8.0).

Figure 3A:
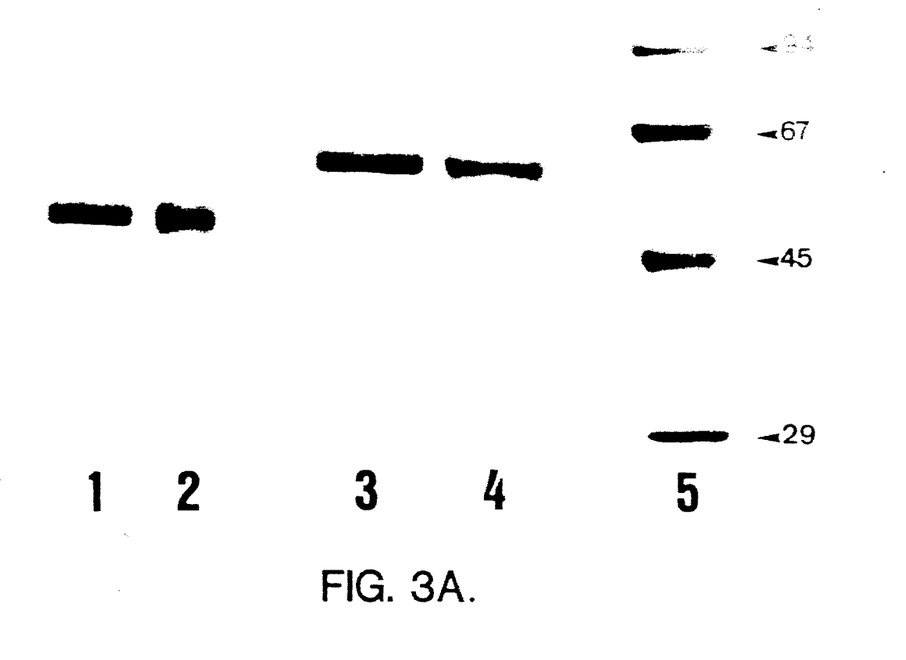
FIG. 3: SDS-PAGE and immunoblots of purified R152E Factor VII. A) SDS-PAGE of R152E Factor VII and wild-type plasma derived Factor VII. Lanes: 1, nonreduced plasma derived Factor VII; 2, nonreduced R152E Factor VII; 3, reduced plasma derived Factor VII; 4, reduced R152E Factor VII; 5, molecular weight standards (phosphorylase b, 94,000; bovine serum albumin, 67,000; ovalbumin, 45,000; carbonic anhydrase, 29,000). B) Immunoblot analysis of R152E and wild-type Factor VII. Lanes: 1, reduced R152E Factor VII; 2, reduced recombinant wild-type Factor VII; 3, reduced plasma-derived Factor VII; 4, unreduced R152E Factor VII; 5, unreduced recombinant wild-type Factor VII; 6, unreduced plasma-derived wild-type Factor VII.
Figure 3B:
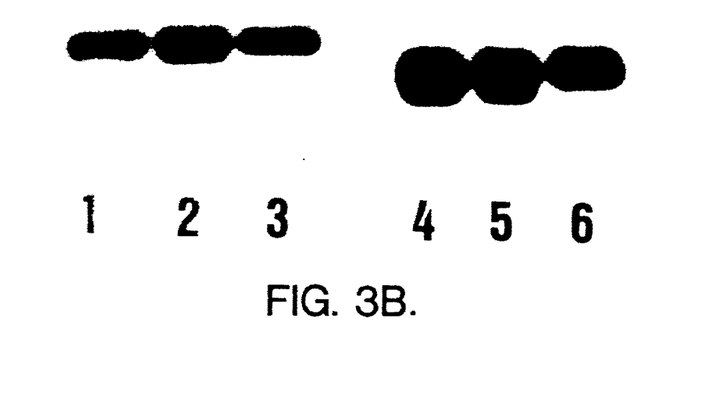

The purified R152E Factor VII migrated as a single band in SDS-polyacrylamide gels stained with Coomassie Blue (FIG. 3A). As can be seen in the SDS gels and immunoblots (FIG. 3B), the molecular weight of R152E Factor VII was indistinguishable from either recombinant wild-type Factor VII (produced in BHK cells generally according to U.S. Pat. No. 4,784,950, incorporated by reference herein) or plasma-derived human Factor VII. The latter was obtained from therapeutic plasmapheresis plasma and was partially purified by a combination of barium citrate adsorption and elution and DEAE-Sepharose CL-6B chromatography generally according to Miletich et al., Meth. Enzymol. 80:221-228 (1981). Factor VII obtained from DEAE-Sepharose chromatography was purified to homogeneity by immunoaffinity chromatography and FPLC chromatography as described in Wildgoose et al., Blood 73:1888-1895 (1989), incorporated herein by reference. The clotting activity of the single chain mutant Factor VII protein was compared to that of recombinant wild-type Factor VII. A one-stage clotting assay was performed essentially as follows: Incubation mixtures consisted of 1.0 μM R152E Factor VII or recombinant wild-type Factor VII; mixed brain phospholipids, 0.5 mM final phospholipid concentration (human brain cephalin, prepared generally according to Bell et al., Nature 174:880-881 (1954) and phospholipid concentrations determined according to Chen et al., Analyt. Chem. 28:1756-1758 (1956)); 100 μl human brain thromboplastin (tissue factor) (Nawroth et al., Thromb. Res. 44:625-637 (1986)); 100 μl Factor VII-deficient plasma and 5 mM CaCl$_2$ (final concentration) in a total volume of 300 μl 0.05M Tris-HCl (pH 7.5) 0.1M NaCl / 0.1% bovine serum albumin (TBS/BSA). Assays were performed in 12×75 mm borosilicate glass tubes incubated at 37° C. for 1-3 min. Clotting times were converted to units of Factor VII activity from a standard curve constructed with 1:5 to 1:200 dilutions of normal pooled human plasma (assumed to contain one unit per ml Factor VII activity; prepared by pooling citrated serum from 20 healthy donors). The results showed that several preparations of purified R152E Factor VII exhibited a low average specific coagulant activity of 0.00025 U/μg (range 0.0001-0.0004 U/μg), or ~0.01% of that observed for recombinant wild-type Factor VII preparations (1.5 U/μg).

To test whether the single-chain R152E Factor VII possessed intrinsic coagulant activity or whether the small amount of activity observed was due to contaminating proteases secreted from the BHK cells or present in the serum component of the culture media, R152E Factor VII was treated with dansyl-Glu-Gly-Arg-Chloromethyl ketone. This serine protease inhibitor does not interact with the single chain form of Factor VII. Williams et al., J. Biol. Chem. 264:7536-7543 (1989). R152E Factor VII (1 μM), wild-type Factor VII (1 μM), and recombinant wild-type Factor VIIa (1 μM) were incubated separately with 0.7 mM dansyl-Glu-Gly-Arg-Chloromethyl ketone (Calbiochem, San Diego, Calif.) at 37° C. for 1 hour in a total volume of 200 μl 0.05M Tris-HCl (pH 7.5)/0.1M NaCl/0.5% BSA. Following incubation, the samples were dialyzed overnight at 4° C. against 2 L of 0.05M Tris-HCl (pH 7.5)/0.1M NaCl to remove the inhibitor.

Following incubation with the inhibitor, R152E Factor VII preparations exhibited no detectable clotting activity, indicating that the R152E Factor VII preparations were contaminated with a serine protease(s) (Table 3). The reduction in activity seen with plasma-derived and recombinant wild-type single-chain Factor VII was attributed to the presence of small quantities of contaminating Factor VIIa in the samples.

TABLE 3

Effect Of Incubating Factor VII With Dansyl-Glutamyl—Glycyl—Arginine Chloromethyl Ketone (DEGRck) Specific Activity

| Protein | −DEGRck | +DEGRck | % Decrease |
|---|---|---|---|
| Plasma FVII | 2.5 U/ug | 0.45 U/ug | 82% |
| Wild-type FVII | 15 U/ug | 0.35 U/ug | 77% |
| Wild-type FVIIa | ~50 U/ug | ND | 100% |
| R152E FVII | 0.0004 U/ug | ND | 100% |

ND = Not Detectable

To determine the effect of the physiological Factor VII activators on R152E Factor VII preparations, R152E Factor VII was incubated with either Factor Xa or Factor IXa. The results of these reactions were monitored by clotting assays and immunoblotting.

The clotting assays were performed generally as described above. Incubation mixtures consisted of 1.0 μM recombinant Factor VII or R152E Factor VII along with mixed brain phospholipids (0.5 mM final phospholipid concentration), 5 mM CaCl$_2$ and either Factor IXa (21 nM) or Factor Xa (20 nM) in a total volume of 200 μl 0.05M TBS/BSA. Factors IX and X were obtained from therapeutic plasmapheresis plasma and were partially purified by a combination of barium citrate adsorption and elution and DEAE-Sepharose CL-6B chromatography generally according to Miletich et al., Meth. Enzymol. 80:221-228 (1981). The Factor X pool obtained from DEAE-Sepharose chromatography was purified to homogeneity by a combination of dextran sulfate agarose (DSA) column chromatography and Sephadex G-150 column chromatography as described by Kondo et al., Blood 70:1947-1954 (1987). Factor X was activated by incubation with insolubilized RVV-X (Stern et al., J. Clin. Invest. 74:1910-1921 (1984)) and separated from any residual Factor X by Sephadex G-100 column chromatography. The final product was homogeneous as assessed by SDS-PAGE and was essentially all Factor Xa. The partially purified Factor IX pool obtained from DEAE-Sepharose chromatography was further purified by DSA column chromatography and immunoaffinity chromatography (Kondo et al, supra.). Human IXa$_\beta$ was prepared by incubating Factor IX with insolubilized RVV-X followed by gel filtration on Sephacryl S-200. Lindquist et al., *J. Biol. Chem.* 253:1902 (1978).

At selected intervals, 10 μl aliquots were removed from the incubation mixtures and diluted (25–100 fold) in TBS/BSA. Aliquots (100 μl) of the diluted samples were then transferred to 12×75 mm borosilicate glass tubes, followed by the addition of 100 μl Factor VII-deficient plasma. To each mixture was added in succession 100 μl of human brain thromboplastin, and 100 μl of 25 mM $CaCl_2$. Clotting times were converted to units of Factor VII activity from a standard curve constructed with 1:5 to 1:200 dilutions of normal pooled human plasma.

Samples were also removed from the clotting assays for immunoblot analysis. As in the clotting assay, 10 μl aliquots were removed at selected intervals and subjected to SDS-PAGE (following reduction with 10% β-mercaptoethanol) using a 2.5% polyacrylamide concentrating gel and a 10% polyacrylamide resolving gel. Following electrophoresis, the proteins were electrophoretically transferred to nitrocellulose membranes, and Factor VII/VIIa degradation products were visualized by incubation with rabbit affinity-purified anti-Factor VII IgG followed by incubation with $^{125}I$-protein A and autoradiography.

Figure 4A:
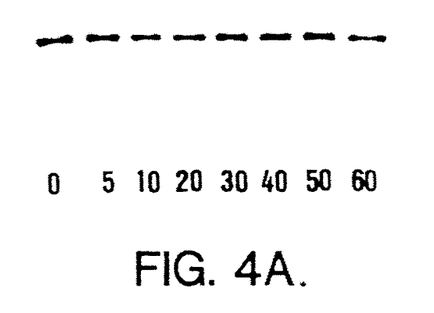
FIG. 4: Immunoblot of the incubation of R152E Factor VII with Factor IXa and Factor Xa. A) Immunoblot analysis of the incubation of R152E Factor VII with Factor IXa. B) Immunoblot analysis of the incubation of R152E Factor VII with Factor Xa. The number beneath each lane represents the time of incubation in minutes.
Figure 4B:
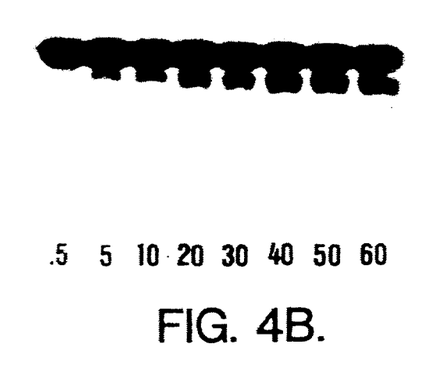

No change in the specific clotting activity or covalent structure (FIG. 4A) of R152E Factor VII was observed when it was incubated with Factor IXa. However, the immunoblots of the Factor Xa-R152E Factor VII incubation mixtures revealed that R152E Factor VII was cleaved, in a time dependant manner, to a slightly lower molecular weight form migrating at around 40 kDa (FIG. 4B). This lower molecular weight form did not correspond to either chain of Factor VIIa and appeared to be a result of a contaminating protease in the Factor Xa preparation. Consistent with previous results (Wildgoose and Kisiel, *Blood* 73: 1888–1895, 1989), the incubation of recombinant Factor VII with either Factor IXa or Factor Xa resulted in a rapid increase in specific activity paralleling the appearance of two-chain Factor VIIa.

EXAMPLE II

Anticoagulant Activity of Modified Factor VII

The ability of the mutant Factor VII (R152E) to compete with wild-type Factor VII for tissue factor and inhibit its clotting activity was assessed in a one-step clotting assay in the presence of limiting amounts of tissue factor (thromboplastin). If the two proteins reacted similarly with the Factor VII co-factor, tissue factor, R152E should inhibit the clotting activity of wild-type Factor VII.

Figure 5:
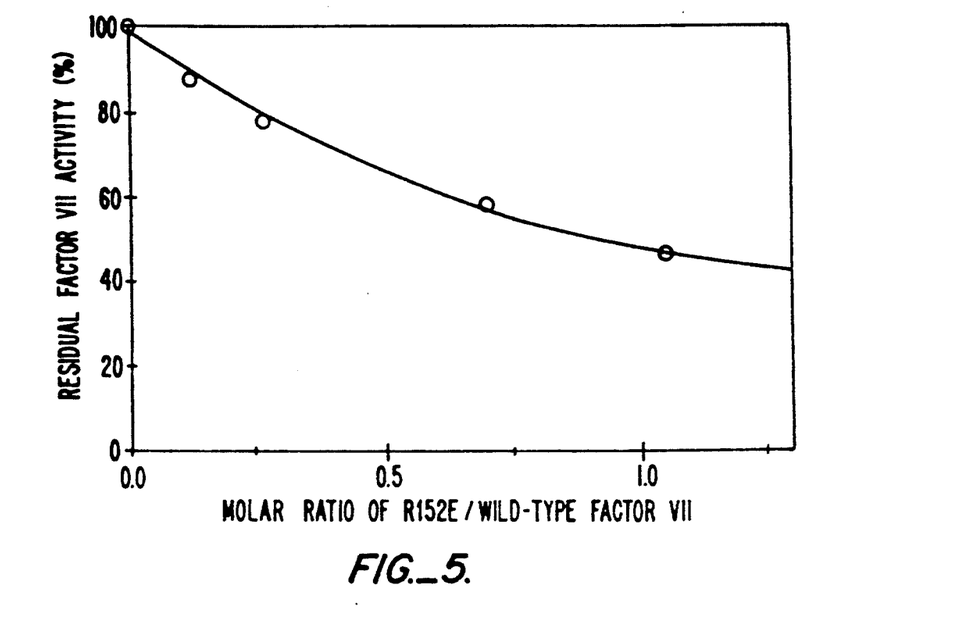
FIG. 5: Inhibition of wild-type Factor VII clotting activity by R152E Factor VII.

In these experiments, various molar ratios of R152E Factor VII and wild-type Factor VII as shown in FIG. 5 were established in 100 μl of TBS/BSA in 10×75 mm borosilicate glass tubes. To each mixture was added, in succession, 100 μl of Factor VII-deficient plasma, 100 μl of thromboplastin, and 100 μl of 25 mM $CaCl_2$. The apparent Factor VII activity in each mixture was corrected for the theoretical decrease in Factor VII activity expected as a result of the reduction in wild-type Factor VII concentration. Thus, residual Factor VII activity was defined as the apparent activity of the combined R152E Factor VII/wild-type Factor VII mixture divided by the activity of an equal fraction containing only wild-type Factor VII at that particular concentration present in the mixture.

In as much as R152E Factor VII possesses no clotting activity, a 1:1 molar ratio of R152E/wild-type Factor VII should exhibit a clotting activity 50% of that observed in an equivalent sample containing only wild-type Factor VII. FIG. 5 illustrates that R152E inhibits wild-type Factor VII clotting activity in this manner. This supports the conclusion that R152E Factor VII appears to interact with tissue factor in a manner very similar to that observed with wild-type Factor VII. Thus the modified R152E Factor VII molecule, with the exception of its activation cleavage site, appears to be structurally very similar to wild-type Factor VII.

EXAMPLE III

$Arg_{152} \rightarrow Leu_{152}$ Factor VII

A DNA sequence coding for the $Arg_{152} \rightarrow Leu$ Factor VII was constructed essentially as described in Example I, with the substitution of oligonucleotides ZC1716 (5' CCC CAA GGC CTG ATT GTG GGG 3') and ZC1718 (5' TTG CCC CCC ACA ATC AGG CCT T 3') for ZC1715 and ZC1714, respectively. The complete coding sequence was assembled in a pDX-based expression vector.

Expression and purification of the $Arg_{152} \rightarrow Leu$ modified Factor VII protein is performed as set forth in Example I above. The ability of the modified protein to compete with wild-type Factor VII for tissue factor and to inhibit clotting activity is determined in clotting assays as described in Example II above.

EXAMPLE IV

Substitution of Gly, Asp and Ile for $Arg_{152}$

In a manner similar to that described in Example I, coding sequences for $Gly_{152}$ Factor VII, $Asp_{152}$ Factor VII, and $Ile_{152}$ are constructed.

The oligonucleotides shown in Table 4 were synthesized according to standard procedures using an Applied Biosystems model 380A DNA synthesizer.

TABLE 4

| Oligonucleotide | Sequence (5'→ 3') |
| --- | --- |
| ZC878 | CCC CAA GGC ATC ATT GTG GGG |
| ZC879 | TTG CCC CCC ACA ATG ATG CCT T |
| ZC1386 | CCC CAA GGC GAC ATT GTG GGG |
| ZC1387 | TTG CCC CCC ACA ATG TCG CCT T |
| ZC1388 | TTG CCC CCC ACA ATC CCG CCT T |
| ZC1389 | CCC CAA GGC GGG ATT GTG GGG |

Oligonucleotide pair ZC879 and 878 is substituted for ZC1714 and 1715 to construct the Ile substitution. Oligonucleotide pair ZC1387 and 1386 is substituted for ZC1714 and 1715 to construct the Asp substitution. Oligonucleotide pair ZC1388 and 1389 is used to construct the Gly substitution. The complete coding sequences are assembled in a pDX-based expression vector.

Expression and purification of the $Arg_{152} \rightarrow Gly$, $Arg_{152} \rightarrow Asp$, and $Arg_{152} \rightarrow Ile$ modified Factor VII proteins is performed similar to that procedure set forth in Example I above. The ability of each of the modified proteins, or in combinations thereof, to compete with wild-type Factor VII for tissue factor and to inhibit clotting activity is determined in clotting assays as described in Example II above.

It is evident from the above results that compositions may be provided of Factor VII which are able to bind tissue factor yet are resistant to cleavage, and thus activation, by plasma activating factors. These results are especially encouraging, in that modified Factor VII molecules may now be employed as therapeutic or prophylactic anticoagulant compositions. In general, the zymogen coagulation factors have significantly longer plasma half-lives than their activated counterparts. The stability of the modified Factor VII in plasma may therefore provide an increased half-life when compared to conventional anticoagulants. As modified Factor VII acts specifically to interrupt the clotting cascade without degrading or consuming clotting factors, it may be expected that administration of modified Factor VII preparations will be accompanied by fewer undesirable side effects than experienced with current therapies. Further, the modified Factor VII may readily be produced by recombinant means. Thus efficacy, convenience and economics of lower dosages and less frequent administration, and a relative lack of toxicity are among the advantages conferred by the compositions of the present invention.

Although the foregoing invention has been described in some detail by way of illustration and example for purposes of clarity of understanding, it will be obvious that certain changes and modifications may be practiced within the scope of the appended claims.

What is claimed is:

1. A polynucleotide molecule comprising two operatively linked sequence coding regions encoding, respectively, a pre-pro peptide and a gla domain of a vitamin K-dependent plasma protein, and a gla domain-less Factor VII having an amino acid substitution in the activation region, wherein said polynucleotide encodes a modified Factor VII molecule that is resistant to activation by plasma Factor Xa, as compared to wild-type Factor VIIa, and is capable of inhibiting the clotting activity of wild-type Factor VIIa.

2. The polynucleotide molecule according to claim 1, wherein the amino acid modification in the activation region is at a cleavage site and comprises substituting Glu, Leu, Asp, Gly, or Ile for $Arg_{152}$.

3. The polynucleotide molecule of claim 1, wherein the Factor VII is human Factor VII.

4. The polynucleotide molecule of claim 1, wherein the pre-pro peptide and gla domain are the pre-pro peptide and gla domain of human Factor VII.

5. The polynucleotide molecule of claim 1, wherein the modified Factor VII molecule encoded thereby competes with wild-type Factor VIIa for binding to tissue factor.

6. A mammalian cell line transfected with the polynucleotide molecule of claim 1, wherein said polynucleotide is DNA.

7. The transfected cell line of claim 6, wherein the cell line is a baby hamster kidney cell line or 293 cell line.

8. The transfected cell line of claim 7, wherein the cell line is BHK 570 having ATCC No. CRL 10314.

* * * * *